(12) United States Patent
Ciesielski et al.

(10) Patent No.: US 7,943,138 B2
(45) Date of Patent: May 17, 2011

(54) SURVIVIN PEPTIDES AS CANCER VACCINES

(75) Inventors: Michael J. Ciesielski, Orchard Park, NY (US); Robert A. Fenstermaker, Orchard Park, NY (US)

(73) Assignee: Health Research, Inc., Buffalo, NY (US)

( * ) Notice: Subject to any disclaimer, the term of this patent is extended or adjusted under 35 U.S.C. 154(b) by 311 days.

(21) Appl. No.: 12/176,052

(22) Filed: Jul. 18, 2008

(65) Prior Publication Data
US 2009/0041732 A1  Feb. 12, 2009

Related U.S. Application Data

(60) Provisional application No. 60/961,206, filed on Jul. 19, 2007.

(51) Int. Cl.
*A61K 35/12* (2006.01)
*A61K 38/08* (2006.01)
*A61K 38/10* (2006.01)
*A61K 38/16* (2006.01)
*A61K 39/00* (2006.01)

(52) U.S. Cl. ............... 424/185.1; 424/93.71; 424/277.1; 435/372; 514/19.3; 514/21.4; 514/21.5; 514/21.6; 530/326; 530/327; 530/328

(58) Field of Classification Search .................. None
See application file for complete search history.

(56) References Cited

U.S. PATENT DOCUMENTS

| | | |
|---|---|---|
| 2004/0176573 A1* | 9/2004 | Thor et al. .................. 530/350 |
| 2006/0073159 A1 | 4/2006 | Vonderheide et al. |
| 2007/0083334 A1* | 4/2007 | Mintz et al. ..................... 702/19 |
| 2007/0104689 A1 | 5/2007 | Gillies et al. |

* cited by examiner

Primary Examiner — Jeffrey E Russel
(74) Attorney, Agent, or Firm — Hodgson Russ LLP

(57) ABSTRACT

Provided are compositions and methods for treating survivin expressing cancers. The compositions contain peptide survivin peptide mimics with improved MHC-I binding characteristics. The method involves administering a survivin peptide mimic with improved MHC-I binding characteristics to an individual to effect inhibition of the growth of survivin expressing cancer cells in the individual.

18 Claims, 13 Drawing Sheets

Figure 2.

Survivin-$_{53\text{-}67/57M}$

MHC class I epitopes (HLA-A*0201)

53-62  55-64
DLAQCFFCFKELEGW → DLAQ*MFFCF*KELEGW
53-61  56-64
(SEQ ID NO:18)  (SEQ ID NO:6)

(C>M at AA 57 increases MHC I binding from 1.78% to 131% in
*in situ* binding assays of the SVN56 core epitope)

SEQUENCE LISTING

```
<160> NUMBER OF SEQ ID NOS: 20

<210> SEQ ID NO 1
<211> LENGTH: 142
<212> TYPE: PRT
<213> ORGANISM: human

<400> SEQUENCE: 1

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
            130                 135                 140

<210> SEQ ID NO 2
<211> LENGTH: 140
<212> TYPE: PRT
<213> ORGANISM: mouse
```

```
<400> SEQUENCE: 2

Met Gly Ala Pro Ala Leu Pro Gln Ile Trp Gln Leu Tyr Leu Lys Asn
1               5                   10                  15

Tyr Arg Ile Ala Thr Phe Lys Asn Trp Pro Phe Leu Glu Asp Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asn Pro Ile Glu Glu His Arg Lys His
65                  70                  75                  80

Ser Pro Gly Cys Ala Phe Leu Thr Val Lys Lys Gln Met Glu Glu Leu
                85                  90                  95

Thr Val Ser Glu Phe Leu Lys Leu Asp Arg Gln Arg Ala Lys Asn Lys
            100                 105                 110

Ile Ala Lys Glu Thr Asn Asn Lys Gln Lys Glu Phe Glu Glu Thr Ala
        115                 120                 125

Lys Thr Thr Arg Gln Ser Ile Glu Gln Leu Ala Ala
    130                 135                 140

<210> SEQ ID NO 3
<211> LENGTH: 23
<212> TYPE: PRT
<213> ORGANISM: human

<400> SEQUENCE: 3

Glu Asn Glu Pro Asp Leu Ala Gln Cys Phe Phe Cys Phe Lys Glu Leu
1               5                   10                  15

Glu Gly Trp Glu Pro Asp Asp
            20

<210> SEQ ID NO 4
<211> LENGTH: 23
<212> TYPE: PRT
<213> ORGANISM: artificial
<220> FEATURE:
<223> OTHER INFORMATION: wild type survivin amino acids 49-71 with C
      to M change at amino acid position 57

<400> SEQUENCE: 4

Glu Asn Glu Pro Asp Leu Ala Gln Met Phe Phe Cys Phe Lys Glu Leu
1               5                   10                  15

Glu Gly Trp Glu Pro Asp Asp
            20

<210> SEQ ID NO 5
<211> LENGTH: 6
<212> TYPE: PRT
<213> ORGANISM: artificial
<220> FEATURE:
<223> OTHER INFORMATION: survivin vaccine core epitope C to M change
      at amino acid 57 of full length survivin

<400> SEQUENCE: 5

Gln Met Phe Phe Cys Phe
1               5

<210> SEQ ID NO 6
<211> LENGTH: 15
<212> TYPE: PRT
<213> ORGANISM: artificial
```

```
<220> FEATURE:
<223> OTHER INFORMATION: survivin amino acids 53-67 with C to M change
      at position 57

<400> SEQUENCE: 6

Asp Leu Ala Gln Met Phe Phe Cys Phe Lys Glu Leu Glu Gly Trp
1               5                   10                  15

<210> SEQ ID NO 7
<211> LENGTH: 8
<212> TYPE: PRT
<213> ORGANISM: human

<400> SEQUENCE: 7

Ser Ile Ile Asn Phe Glu Lys Leu
1               5

<210> SEQ ID NO 8
<211> LENGTH: 8
<212> TYPE: PRT
<213> ORGANISM: human

<400> SEQUENCE: 8

Ala Trp Gln Pro Phe Leu Lys Asp
1               5

<210> SEQ ID NO 9
<211> LENGTH: 8
<212> TYPE: PRT
<213> ORGANISM: human

<400> SEQUENCE: 9

Arg Ile Ser Thr Phe Lys Asn Trp
1               5

<210> SEQ ID NO 10
<211> LENGTH: 8
<212> TYPE: PRT
<213> ORGANISM: human

<400> SEQUENCE: 10

Ala Glu Ala Gly Phe Ile His Cys
1               5

<210> SEQ ID NO 11
<211> LENGTH: 8
<212> TYPE: PRT
<213> ORGANISM: human

<400> SEQUENCE: 11

Cys Phe Phe Cys Phe Lys Glu Leu
1               5

<210> SEQ ID NO 12
<211> LENGTH: 8
<212> TYPE: PRT
<213> ORGANISM: human

<400> SEQUENCE: 12

Ser Gly Cys Ala Phe Leu Ser Val
1               5

<210> SEQ ID NO 13
<211> LENGTH: 8
<212> TYPE: PRT
<213> ORGANISM: artificial
```

```
<220> FEATURE:
<223> OTHER INFORMATION: SVN-L82 S to L change

<400> SEQUENCE: 13

Leu Gly Cys Ala Phe Leu Ser Val
1               5

<210> SEQ ID NO 14
<211> LENGTH: 7
<212> TYPE: PRT
<213> ORGANISM: human

<400> SEQUENCE: 14

Thr Leu Gly Glu Phe Leu Lys
1               5

<210> SEQ ID NO 15
<211> LENGTH: 10
<212> TYPE: PRT
<213> ORGANISM: artificial
<220> FEATURE:
<223> OTHER INFORMATION: C to M change at position 57

<400> SEQUENCE: 15

Ala Gln Met Phe Phe Cys Phe Lys Glu Leu
1               5                   10

<210> SEQ ID NO 16
<211> LENGTH: 9
<212> TYPE: PRT
<213> ORGANISM: artificial
<220> FEATURE:
<223> OTHER INFORMATION: C to M change at position 57

<400> SEQUENCE: 16

Gln Met Phe Phe Cys Phe Lys Glu Leu
1               5

<210> SEQ ID NO 17
<211> LENGTH: 8
<212> TYPE: PRT
<213> ORGANISM: artificial
<220> FEATURE:
<223> OTHER INFORMATION: SVN-57-64 with C to M change at position 57

<400> SEQUENCE: 17

Met Phe Phe Cys Phe Lys Glu Leu
1               5

<210> SEQ ID NO 18
<211> LENGTH: 15
<212> TYPE: PRT
<213> ORGANISM: human

<400> SEQUENCE: 18

Asp Leu Ala Gln Cys Phe Phe Cys Phe Lys Glu Leu Glu Gly Trp
1               5                   10                  15

<210> SEQ ID NO 19
<211> LENGTH: 10
<212> TYPE: PRT
<213> ORGANISM: human

<400> SEQUENCE: 19

Ala Gln Cys Phe Phe Cys Phe Lys Glu Leu
1               5                   10
```

```
<210> SEQ ID NO 20
<211> LENGTH: 9
<212> TYPE: PRT
<213> ORGANISM: human

<400> SEQUENCE: 20

Gln Cys Phe Phe Cys Phe Lys Glu Leu
1               5
```

SURVIVIN PEPTIDES AS CANCER VACCINES

This application claims priority to U.S. application Ser. No. 60/961,206, filed on Jul. 19, 2007, the disclosure of which is incorporated herein by reference.

This invention was supported by Government funds under grant no. NS049309-02 from the National Institutes of Health. The Government has certain rights in the invention.

FIELD OF THE INVENTION

The present invention relates generally to cancer vaccines and more specifically to modified survivin peptides for use as cancer vaccines.

BACKGROUND OF THE INVENTION

Survivin is a 16.5 kDa intracellular protein that belongs to the inhibitor of apoptosis protein (IAP) family. Survivin acts in concert with the mitotic spindle apparatus to regulate cell division. It is expressed in certain cells during the G2/M phase of the cell cycle and associates with the spindle microtubule organizing center during this phase of cell cycle progression [Zhao J, et al. (2000) J Cell Sci, 113:4363-71; Li F, et al. (1998) Nature, 396:580-4; Fortugno P, et al. (2002) J Cell Sci, 115:575-85]. Survivin has also been shown to modulate the function of certain caspases, directly inhibiting apoptosis [Tamm I, et al. (1998) Cancer Res, 58:5215-20; Conway et al. (2000) Blood 95:1435-42; Shin S, et al. (2001) Biochemistry, 40:1117-23]. In addition, survivin inhibits the cyclin D/cdk4 complex [Fukuda S, Pelus L M. (2002) Cell Cycle, 1(5):322-6], permitting cell cycle progression. Thus, survivin functions in critical roles at a number of different cellular loci to regulate the cell cycle and to inhibit apoptotic cell death.

Survivin is overexpressed during the G(2)/M phase of the cell cycle in most cancer cells and is one of the most specific cancer antigens identified to date. It is expressed in a large percentage of tumors and is rarely detectable in normal adult tissues [Overwijk W W, et al. (1998) J Exp Med, 188:277-86; Adida C, et al. (1998) Am J Pathol 152:43-49]. Although survivin is expressed in some instances within CD34(+) hematopoietic stem and progenitor cells that have been stimulated by hematopoetic growth factors, it is generally not presented on the surface of these cells. [Fukuda S, Pelus L M. (2002) Cell Cycle. 1(5):322-6].

In addition to many other cancers, survivin expression occurs commonly in malignant gliomas where it is associated with a poor prognosis [Kajiwara Y, et al. (2003) Cancer 97:1077-1083; Sasaki T, (2002) Acta Neuropathol (Berl) 104: 105-109; Chakravarti A, et al. (2002) J Clin Oncol, 20:1063-8]. Since survivin is expressed by many different cancer types, and consequently, its use as a tumor vaccine target has broad implications for anticancer vaccine therapy. However, previous studies have not identified survivin peptides that are effective when administered following tumor challenge. Further, little data is available concerning the potential effectiveness of survivin peptides in humans. Therefore, there is an ongoing need for survivin peptides that can elicit strong cellular immune responses for use as anti-survivin cancer immunotherapies.

SUMMARY OF THE INVENTION

The present invention provides compositions and methods for treating cancers that express survivin. The compositions comprise survivin peptide mimics that contain a cysteine to methionine alteration at amino acid position 57 of the wild type survivin protein sequence. The peptides are 9-23 amino acids in length and have the sequence of SEQ ID NO:4 (ENEPDLAQMFFCFKELEGWEPDD) or a fragment thereof, wherein the fragment comprises at least 9 contiguous amino acids of SEQ ID NO:4, and wherein the fragment also comprises the sequence of SEQ ID NO:5 (QMFFCF). The peptides are capable of stimulating an improved human cell mediated immune response against survivin expressing human cancer cells, as compared to the cell mediated immune response elicited by peptides having the wild type survivin sequence. The peptides are also demonstrated to confer extended survival in a mouse model of glioma.

The method of the invention comprises administering to an individual diagnosed with or suspected of having a survivin expressing cancer a composition comprising a peptide of the invention such that growth of the cancer is inhibited.

Also provided is a substantially purified population of mammalian dendritic cells that are loaded with a peptide of the invention.

BRIEF DESCRIPTION OF THE FIGURES

FIG. 2 provides a graphical comparison of wild type and altered peptide sequences showing MHC class I (HLA-A*0201) epitopes in boxes. A sequence common to all the peptides of the invention (QMFFCF) (SEQ ID NO:5) is italicized in Survivin-53-67/57M.

FIG. 6C provides a graphical representation of data for specific HLA-A*0201 pentamer binding of wild type and altered survivin peptide epitopes.

DESCRIPTION OF THE INVENTION

The present invention provides compositions and methods for inhibiting growth of cancer cells that express survivin. The compositions of the invention comprise survivin peptide mimics that elicit strong antitumor cell-mediated immunity capable of inhibiting the growth of tumors that contain survivin expressing cancer cells. The method of the invention comprises administering to an individual diagnosed with or suspected of having a survivin expressing cancer a peptide mimic of the invention in an amount effective to inhibit growth of the survivin expressing cancer cells in the individual. Inhibition of growth as used herein can include reduction of the size of an existing tumor.

The method of the invention stimulates a cell mediated immune response to survivin expressing cancer cells. In connection with generation of cell mediated immunity, it is considered that a robust cellular immune response generally requires a peptide epitope to be displayed at the surface of an antigen presenting cell (APC) bound to MHC class I molecule, which can trigger a CD8+ T cell response (cytotoxic T cell or CTL). To sustain itself, the CTL immune response is preferably supported through presentation of peptide epitopes bound to MHC class II molecules to cytokine-secreting CD4+ T cells (T helper cells). While some survivin peptides have been shown to elicit CTL responses, attempts to provide viable peptide vaccine candidates from the region of survivin from amino acid numbers 53-67 have failed, possibly due to a lack of HLA*0201 binding ability [Bachinsky M M, et al. (2005) Cancer Immun. 22; 5:6].

The present invention overcomes these and other limitations by providing peptides derived from wild type survivin sequence, wherein the peptides comprise an altered amino acid sequence that improves MHC I binding properties so that the peptides are more effective than wild type peptides at eliciting human CTL responses against survivin-expressing cancer cells.

The complete amino acid sequence of human and mouse survivin proteins are provided as SEQ ID NO:1 and SEQ ID NO:2, respectively. The human and mouse sequences are 100% homologous between amino acids 31 and 71.

The peptides provided in the invention are fragments of full length survivin. The fragments and can range in size from 9-23 amino acids. SEQ ID NO:3 (ENEPDLAQCFFCFKELEGWEPDD) consists of wild type survivin amino acids 49-71.

Each 9-23 amino acid peptide of the invention comprises a cysteine to methionine (C to M) change at amino acid position 57 of the wild type survivin protein sequence.

Figure 1:
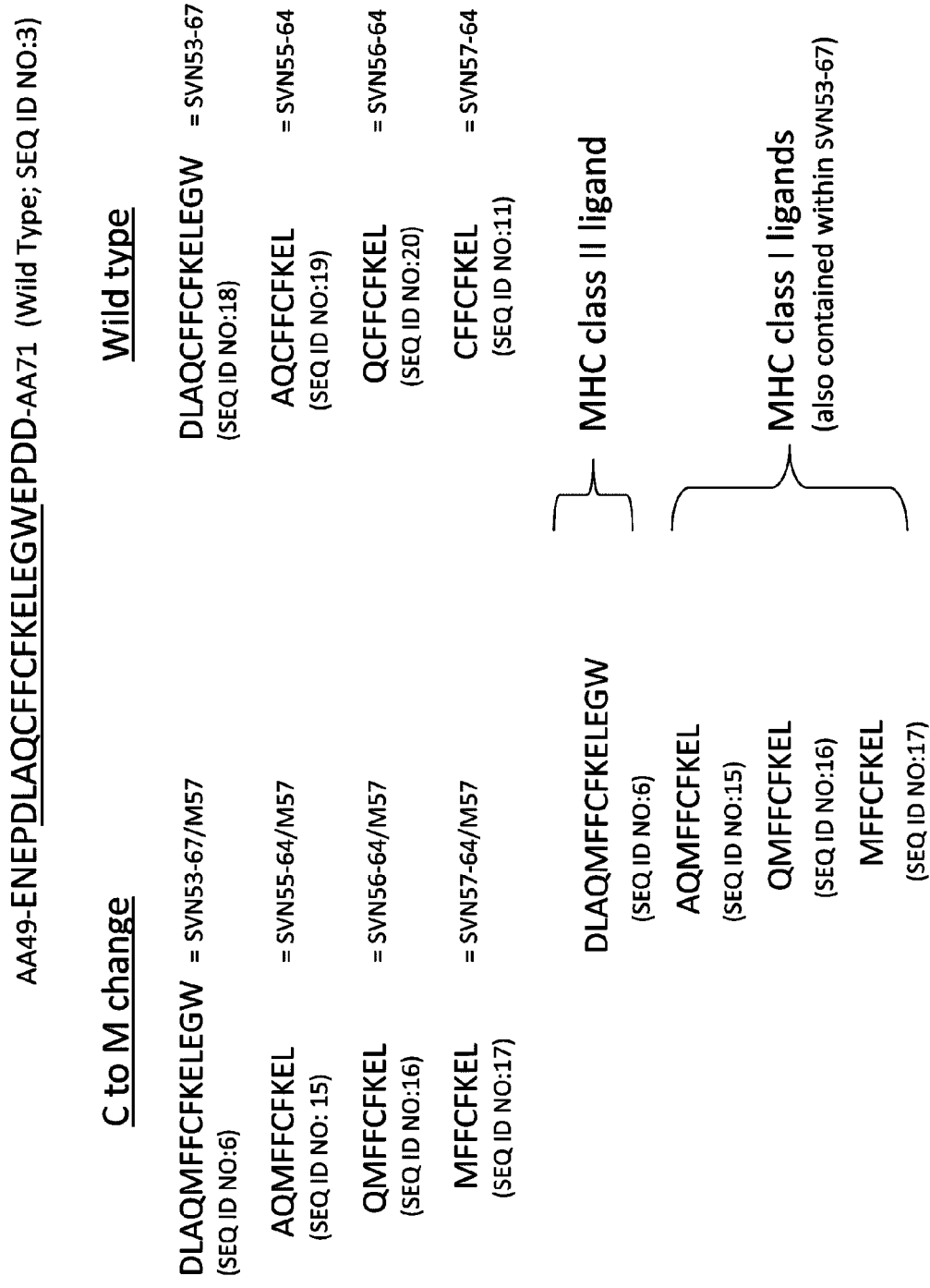
FIG. 1 provides a summary of wild type and altered peptide sequences utilized in the present invention.

SEQ ID NO:4 (ENEPDLAQMFFCFKELEGWEPDD) is a 23 amino acid peptide consisting of wild type survivin amino acids 49-71, but for a C to M alteration at amino acid position 57 of full length survivin (the C to M alteration is present at amino acid number 9 of SEQ ID NO:4). The peptides of the invention can consist of from 9-23 contiguous amino acids of SEQ ID NO:4, including all integers between 9-23 amino acids, wherein the peptides include the C to M alteration at amino acid position 57 of full length survivin. Each peptide of the invention also comprises the core sequence of SEQ ID NO: 5 (QMFFCF). Representative survivin peptides and nomenclature used herein for the peptides are provided in FIG. 1.

Some non-limiting examples of peptides provided by the invention are also depicted in FIG. 2, wherein the core epitope sequence of SEQ ID NO:5 is shown boxed and italicized in context of longer suitable peptide sequences, also boxed, in the peptide shown on the right of FIG. 2. Accordingly, each of the boxed sequences that include the italicized core sequence are sequences of peptides included within the scope of the invention.

In one embodiment, a peptide of the invention consists of SEQ ID NO:6 (DLAQMFFCFKELEGW). This peptide is referred to alternatively as "SVN53-67/M57", "Survivin M57" and "M57." SVN53-67/M57 contains epitopes for binding human MHC I molecules and epitopes capable of binding human MHC II molecules to elicit CD4+ helper T cell responses.

Without intending to be bound by any particular theory, it is believed that the change of C to M in the peptides of the present invention allows for improved presentation of the MHC I binding epitopes to the human immune system, in part via more effective anchoring to MHC I, resulting in a longer association period between the peptide, the MHC I molecule and possibly T cell receptors, and thus, a more robust immune response. Shorter peptides can bind MHC I exclusively. Larger peptides, such as the 15-mer SVN53-67/M57, are designed to bind MHC class II, in addition to MHC class I.

Figure 6:
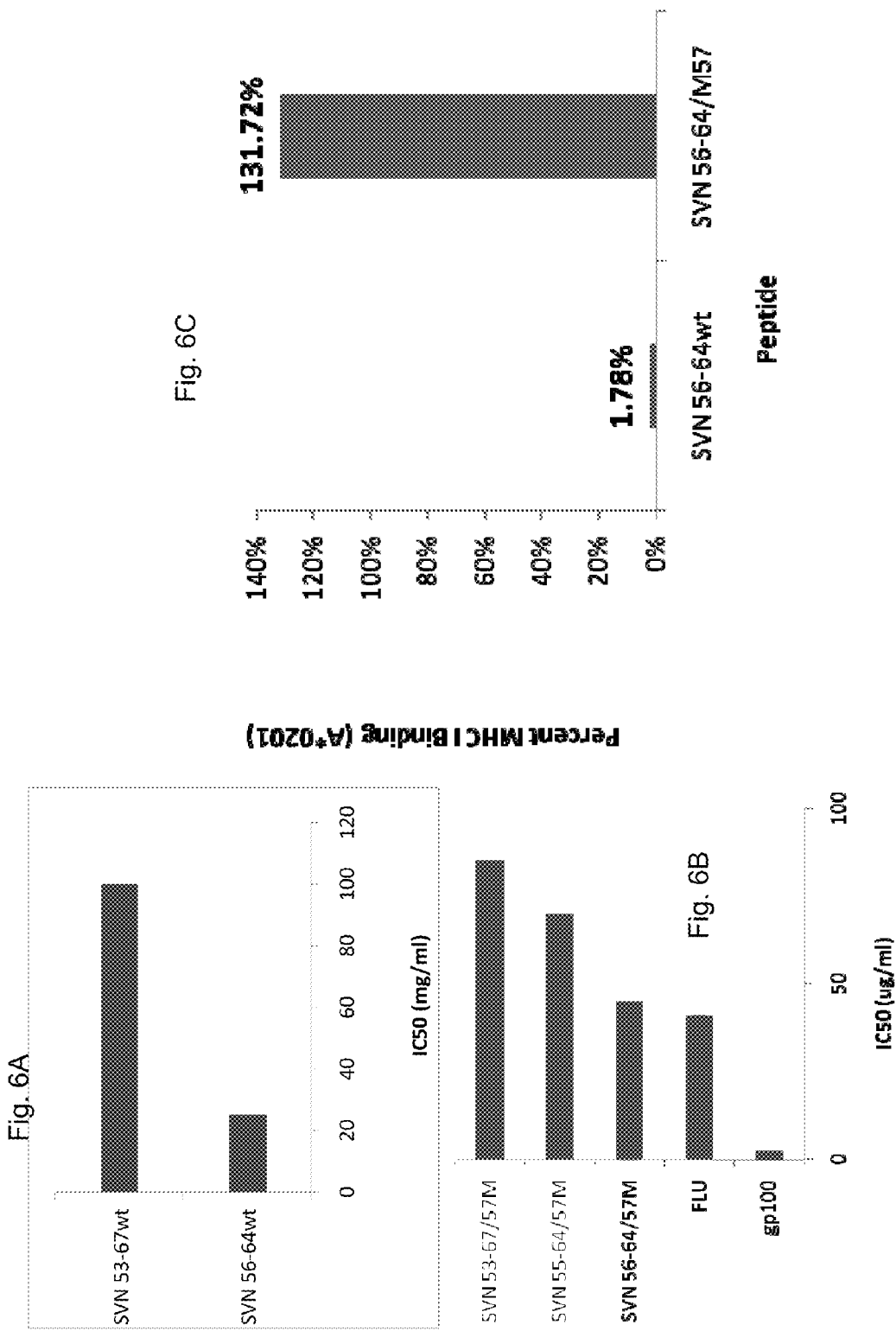
FIGS. 6A, 6B and 6C provide a graphical representations of data from an analysis of HLA-A*0201 binding properties of survivin peptides. To obtain the data summarized in FIGS. 6A and 6B, survivin peptide epitopes were used in MHC class I peptide competitive displacement assays. IC50 represents the 50% inhibition concentration of survivin peptide required to displace a fluorescently labeled-known human MHC Class I ligand (HPV18-27). Positive control peptides (Flu & gp100) represent known immunogenic MHC class I ligands. Data represent mean fluorescence±S.E.M. of triplicate samples.
Figure 7:
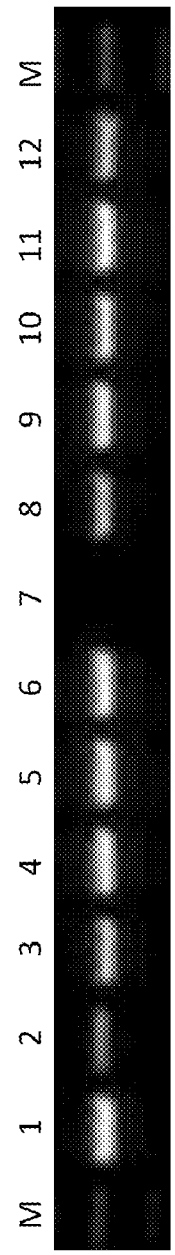
FIG. 7 provides a photographic representation of electrophoretic separation of RT-PCR amplification of survivin mRNA from human glioma specimens. RNA was isolated from cellular lysates of human gliomas and amplified using RT-PCR. The expected sized survivin band was abundantly detected in 11/12 samples as well as controls (M). The control band was derived from PCR of a survivin cDNA FIG. 8 provides a graphical representation of data obtained from ex vivo T cell stimulation via survivin-loaded autologous dendritic cells challenged with an allogeneic mismatched U87 glioma (HLA-A*03 T cells vs. HLA-A*02 glioma; Allo-mis-match).
Figure 8:
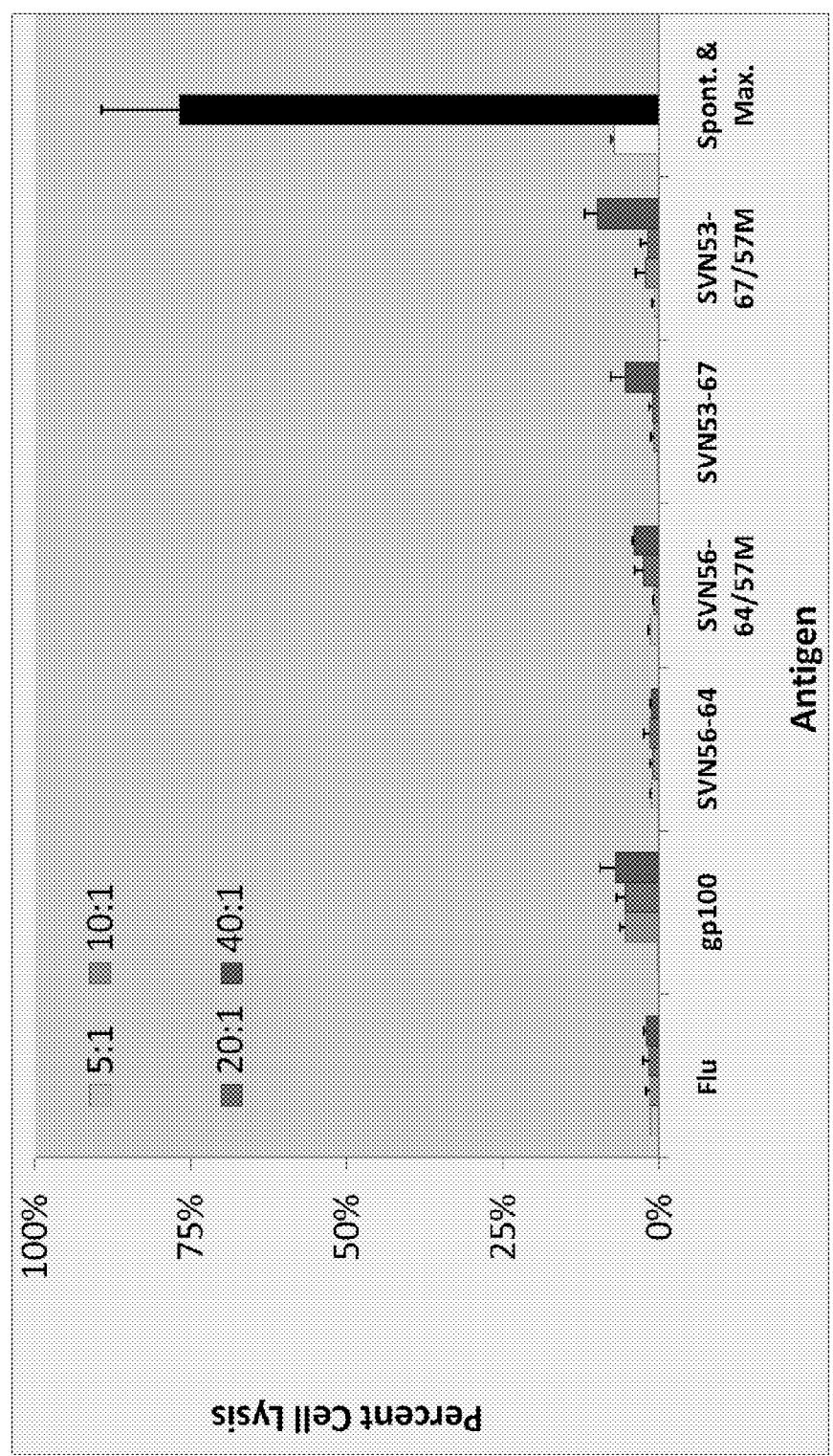

We demonstrate that the C to M amino acid substitution in SVN53-67/M57 increases MHC I binding by approximately 73 fold in in situ binding assays for HLA-A*0201 relative to the wild type sequence (summarized FIG. 2 and FIG. 6C). We have also determined that peptides comprising the C to M change can be used to effectively stimulate CD8+ CTLs, to stimulate CD4+ T cell derived cytokine support, to enhance survival (and potentially be curative for glioma) in a mouse model of brain cancer, as well as elicit a strong ex vivo lytic response against human glioma and CNS lymphoma specimens. Therefore, it is expected that the peptides of the invention can be used in methods for eliciting enhanced MHC-I binding and improved CTL activity against survivin-expressing cancer cells when used as a vaccine in vivo in humans because of concomitantly improved association between the epitopes of the processed peptide and MHC-I anchor residues.

SVN 53-67 peptides (with or without the C to M change) are expected to bind numerous MHC Class I & II molecules that collectively represent a large patient population (Table 1).

TABLE 1

| MHC Class I | | MHC Class II |
|---|---|---|
| HLA-A*0201 | HLA-B*08 | HLA-DRB1*0301 (DR17) |
| HLA-A*03 | HLA-B*1501 (B62) | HLA-DRB1*0401 (DR4Dw4) |
| HLA-A*1101 | HLA-B*1510 | HLA-DRB1*0701 |
| HLA-A*2402 | HLA-B*18 | HLA-DRB1*1501 (DR2b) |
| HLA-A*2402 | HLA-B*2705 | |
| HLA-A*26 | HLA-B*2709 | |
| HLA-A*6801 | HLA-B*3901 | |
| HLA-B*0702 | HLA-B*4402 | |
| HLA-B*08 | HLA-B*5101 | |
| HLA-B*1402 | | |

The peptides of the invention can be prepared by any technique known to those skilled in the art or by techniques hereafter developed. For example, the peptides can be prepared using the solid-phase synthetic technique (Merrifield, J. Am. Chem. Soc., 15:2149-2154 (1963); M. Bodanszky et al., (1976) Peptide Synthesis, John Wiley & Sons, 2d Ed.; Kent and Clark-Lewis in Synthetic Peptides in Biology and Medicine, p. 295-358, eds. Alitalo, K., et al. Science Publishers, (Amsterdam, 1985). The synthesis of peptides by solution methods may also be used, as described in The Proteins, Vol. II, 3d Ed., p. 105-237, Neurath, H., et al., Eds., Academic Press, New York, N.Y. (1976). The synthesized peptides may be substantially purified by preparative high performance liquid chromatography or other comparable techniques available in the art. The composition of the synthetic peptides can be confirmed by an technique for amino acid composition analysis.

The peptides of the present invention may be formulated with a suitable adjuvant in order to enhance the immunological response. Suitable adjuvants include but are not limited to mineral salts, including aluminium hydroxide and aluminium and calcium phosphate gels, oil emulsions and surfactant based formulations, saponin, AS02 [SBAS2] (oil-in-water emulsion), Montanide ISA-51 and ISA-720, particulate adjuvants, including virosomes, AS04, [SBAS4] A1 salt with MPL, ISCOMS (structured complex of saponins and lipids), polylactide co-glycolide (PLG), natural and synthetic microbial derivatives, lipoidal immunostimulators OM-174 (lipid A derivative), synthetic oligonucleotides containing immunostimulatory CpG motifs, modified bacterial toxins, endogenous human immunomodulators, including hGM-CSF and hIL-12, hIL-15, hIL-17, hIL-21, Immudaptin and inert vehicles, including gold particles. The peptides can be administered in a conventional dosage form prepared by combining the peptides with a standard pharmaceutically acceptable carrier according to known techniques. Some examples of pharmaceutically acceptable carriers can be found in: *Remington: The Science and Practice of Pharmacy* (2005) 21st Edition, Philadelphia, Pa. Lippincott Williams & Wilkins.

In one embodiment, the peptides of the invention may be conjugated to an immunogenic carrier protein. Suitable carriers include but are not limited to Limulus polyphemus hemocyanin (LPH), Tachypleus tridentatus hemocyanin (TTH), and bovine serum albumin (BSA), tetanus toxoid and diphtheria toxin, DHBcAg, polyribotol ribosyl phosphate (PRP), PncPD11, and nanoparticle formulations.

In one embodiment, a suitable immunogenic carrier protein is Keyhole Limpet Hemocyanin (KLH).

The peptides of the invention may also be administered as peptide loaded dendritic cells. Thus, the method includes administering to the individual dendritic cells that have been incubated with a peptide of the invention such that the dendritic cells have taken up the peptide to obtain peptide loaded dendritic cells that facilitate presentation of MHC epitope(s) present in the peptide. The dendritic cells employed for this purpose may be isolated from the individual to whom they are to be delivered after incubation with the peptide, or they may be obtained from an allo-matched individual. Accordingly, the invention also provides a composition comprising a substantially purified population of mammalian dendritic cells, wherein the dendritic cells have been incubated with a peptide of the invention such that the dendritic cells take up the peptide.

Various methods known to those skilled in the art may be used to introduce the compositions of the invention to an individual. These methods include but are not limited to intracranial, intrathecal, intradermal, intramuscular, intraperitoneal, intravenous, subcutaneous, oral and intranasal routes.

It will be recognized by those of skill in the art that the form and character of the particular dosing regime employed in the method of the invention will be dictated by the route of administration and other well-known variables, such as the size of the individual and the stage of the disease. Based on such criteria and on the data presented herein, one skilled in the art can determine an amount of peptide effective to inhibit growth of survivin expressing cancer cells for any particular individual. It is generally considered that the amount of peptide administered will range from microgram to milligram amounts.

The method of the invention can be performed in conjunction with conventional anti-cancer therapies. Such therapies can include but are not limited to chemotherapies, surgical interventions, and radiation therapy. The compositions of the invention can be administered prior to, concurrently, or subsequent to such anti-cancer therapies.

The following Examples are meant to illustrate, but not to limit the present invention.

Example 1

This Example provides an in vitro analysis of selected survivin peptide epitopes predicted by SYFPEITHI analysis to bind MHC class I molecules (Table 2). Positive control peptide (OVA-258) represents a known immunogenic MHC class I ligand with a score indicating strong potential binding. Underlined amino acid residues represent MHC I anchor positions.

TABLE 2

| Predicted H-2K$^b$ Binding position | Epitope | | | | | | | | | Score |
|---|---|---|---|---|---|---|---|---|---|---|
| OVA-258 | S | I | I | N | F | E | K | L | (SEQ ID NO: 7) | 25 |
| SVN-9 | A | W | Q | P | F | L | K | D | (SEQ ID NO: 8) | 12 |
| SVN-18 | R | I | S | T | F | K | N | W | (SEQ ID NO: 9) | 13 |
| SVN-39 | A | E | A | G | F | I | H | C | (SEQ ID NO: 10) | 12 |
| SVN-57-64 | C | F | F | C | F | K | E | L | (SEQ ID NO: 11) | 20 |
| SVN-57-64/M57 | M | F | F | C | F | K | E | L | (SEQ ID NO: 17) | 20 |
| SVN-82 | S | G | C | A | F | L | S | V | (SEQ ID NO: 12) | 18 |
| SVN-L82 | L | G | C | A | F | L | S | V | (SEQ ID NO: 13) | 18 |
| SVN-97 | T | L | G | E | F | L | K | L | (SEQ ID NO: 14) | 22 |

Figure 3:
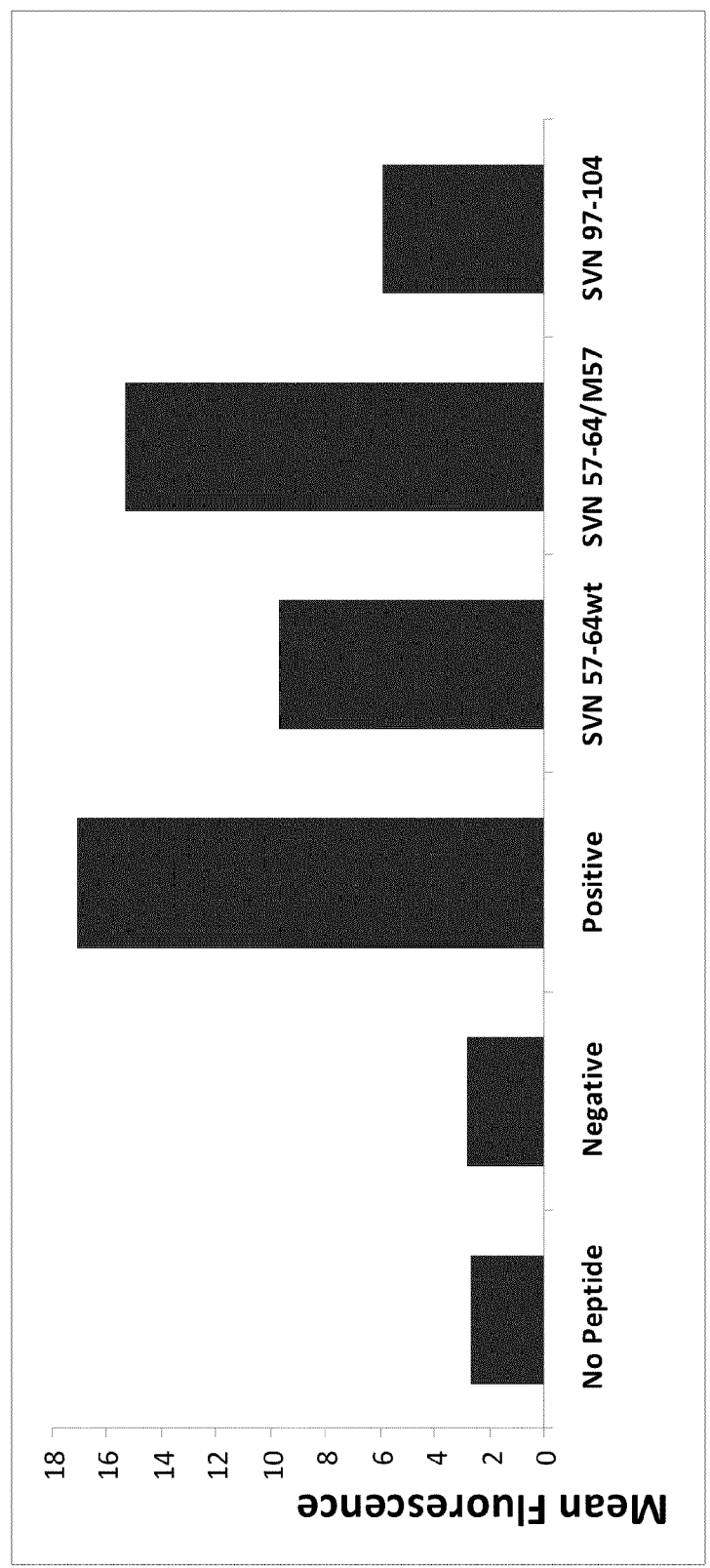
FIG. 3 provides a graphical representation of in vitro test data obtained from survivin peptide binding assays.

In vitro test data for peptide binding assays is presented in FIG. 3. To obtain the data presented in FIG. 3, survivin peptide epitopes were used in conventional MHC class I peptide binding assays. Mean fluorescence in FIG. 3 represents binding of SVN peptides to H2-$K^b$. Upregulation of H2-$K^b$ molecules on the surface of murine RMA-S cells which are deficient in the expression of surface MHC class I molecules was used to determine actual survivin peptide binding in vitro. Data presented in FIG. 3 represent the binding of 100 μM peptide at 37° C. The negative control is an irrelevant peptide that does not bind MHC class I. Data represent mean fluorescence±S.E.M. of triplicate samples.

As can be seen from the data presented in FIG. 3, computer analysis is insufficient to reliably predict the effect of altered peptide sequences on MHC binding strength. Notably, $SVN_{97-104}$ is a peptide that is currently in clinical trials but exhibits binding that is less than SVN 57-64 wt, and considerably less than SVN 57-64/M57, despite the data in Table 2 indicating $SVN_{97-104}$ should exhibit stronger binding than either the wild type or mutant SVN 57-64 peptide. Further, while other changes to amino acids may also enhance binding, we have determined that changes to amino acid anchor positions 57, 59, and 64 (including the changes 57C>L, 59F>Y, and 64L>V) do not improve the immune response to the peptides, despite computer analysis predicting improved MHC retention compared to the wild type sequence. Additionally, we have also determined that the mere substitution of a methionine for an amino acid in the MHC class I first anchor position does not necessarily result in enhanced survivability in a mouse model of intracranial glioma, as evidenced by our analysis of a survivin nonapeptide comprising an S to M change at survivin amino acid position 82.

Example 2

This Example demonstrates the efficacy of the method of the invention in treating a mouse model of intracranial glioma.

To evaluate the capability of the peptides of the invention to elicit an immune response against cancer cells that express survivin, we used what is believed to be the most stringent model available to test vaccine efficacy against glioma. In this regard, the growth of intracranial tumors is widely known to be very difficult to inhibit, especially with cancer vaccines, since results obtained for subcutaneous tumors are not often reflected in intracranial effectiveness. The inhibited growth of intracranial tumors in response to multiple M57 based peptide strategies supports a valid anti-neoplastic effect of the present invention.

Unless otherwise specified, the data presented in this Example were generated using the syngeneic GL261-C57BL/6 murine intracranial glioma model. The intracerebral GL261 glioma model is characterized by a narrow survival window, high initial survival and consistent reproducibility.

The following materials and methods were employed to obtain the data presented in this Example.

Cell lines and culture conditions. GL261 murine glioma cells are grown on 100-mm tissue culture plates in complete Dulbecco's modified Eagle's medium (DMEM) containing 10% fetal calf serum, 5,000 units penicillin/streptomycin, 50 μM 2-mercaptoethanol, 25 mM HEPES, and 1× non-essential amino acids at 37° C. in 5% $CO_2$ with media changes two to three times per week. The DC2.4 dendritic cell line was cultured at a density of $2\times10^6$ cells/ml in RPMI containing 10% fetal calf serum, 5,000 units penicillin/streptomycin, 50 μM 2-mercaptoethanol, 25 mM HEPES, 1× non-essential amino acids and 20 ng/ml GM-CSF (PeproTech, Rocky Hill, N.J.). GL261 murine glioma cells were grown on 100-mm tissue culture plates in complete Dulbecco's modified Eagle's medium (DMEM) containing 10% fetal calf serum, 5,000 units penicillin/streptomycin, 50 μM 2-mercaptoethanol, 25 mM HEPES, and 1× non-essential amino acids at 37° C. in 5% $CO_2$ with media changes two to three times per week.

Peptides. Peptide synthesis was performed using Fmoc chemistry and a solid support resin (Sigma-Genosys, The Woodlands, Tex.). Each peptide was stored at −20° C. until use and diluted in DMSO. An ovalbumin (OVA) peptide sequence SIINFEKL (SEQ ID NO:7) was used as a control.

Immunization of mice with peptide-loaded DCs. Peptide-loaded dendritic cells (DC) are generated from either the DC2.4 cell line or harvested bone marrow derived dendritic cells (BMDC) growing in culture as previously described in, for example, Ciesielski et al. Cancer Immunol Immunother. 2006 Vol. 12, pp 1491-503. BMDCs are harvested from the long bones of euthanized 6-week-old C57BL/6 mice and cells are cultured at a density of $2\times10^6$ cells/ml in RPMI containing 10% fetal calf serum, 5,000 U penicillin/streptomycin, 50 μM 2-mercaptoethanol, 25 mM HEPES, 1× non-essential amino acids and 20 ng/ml GM-CSF (PeproTech, Rocky Hill, N.J., USA). After 48 hours, non-adherent cells are removed and medium containing GM-CSF is replenished. After 6 days, non-adherent cells are harvested for peptide loading. DC2.4 cells and BMDC are loaded with 40 μg of each peptide added to individual wells containing $3\times10^6$ DC per ml. Peptides and DC are incubated at 37° C. for 2 hours, harvested, washed and re-suspended in PBS. A total of $1\times10^6$ DC are generally used to vaccinate each animal via the subcutaneous route. Booster vaccines of the same composition are provided every 7 days, depending on survival.

Splenocyte and T cell isolation. Splenic tissue of vaccinated C57BL/6 mice is harvested at endpoint sacrifice. Cells are teased from mouse spleens with sterile forceps and passed through a 70 μm filter. (BD Falcon). Splenocytes are cultured in DMEM containing 10% fetal bovine serum, IL-2 (10 units/ml) and IL-7 (1 ng/ml). Medium is replenished on days 2 and 7. To isolate T cells, splenocytes are centrifuged for 5 min and the pellet is re-suspended in RBC lysis buffer (R&D Systems). Cells are washed twice and re-suspended in complete RPMI culture medium.

Tumor cell lysis by CTL. Cellular assays for specific T cell lysis of target tumor cells is performed using the Live/Dead cell mediated cytoxicity kit (Molecular Probes-Invitrogen). GL261 cells are trypsinized and suspended at $1\times10^6$ cells/ml followed by addition of 10 μl $DiOC_{18}$ label (green fluorescence) for 20 min at 37° C. After labeling, cells are centrifuged, washed in PBS twice, and resuspended at $1\times10^6$ cells/ml of DMEM. Next, $1\times10^4$ GL261 $DiOC_{18}$-labeled target cells are added to individual culture tubes. Splenocytes from vaccinated animals are added to the target cells in ratios ranging from 1:25 to 1:100 for 2 hours at 37° C. Conditions are also set up to assay background levels, spontaneous membrane integrity loss and maximal lysis. Propidium Iodide is added to each tube to label cells with permeated cell membranes red. Cells are pelleted and used for FACS analysis. Percentage cytotoxicity is calculated using the formula: (experimental PI-$DiOC_{18}$ cells−spontaneous)/(maximum PI-$DiOC_{18}$−spontaneous PI-$DiOC_{18}$)×100. Maximum release is determined by repeated freeze-thawing of $DiOC_{18}$ labeled target cells. Spontaneous release is measured by incubating PI-$DiOC_{18}$ cells in the absence of effector cells. Data is analyzed using FCS Express software. Analysis is based upon gating on GL261 cells to eliminate any background from effector cells.

Intracerebral GL261 tumor cell injection and survival analysis. Male C57BL/6 mice are anesthetized with an intraperitoneal (i.p.) injection of ketamine (80 mg/kg) and xylazine (20 mg/kg) and fixed in a stereotactic head frame (David Kopf Instruments, Tujunga, Calif.). A midline scalp incision is made and the bregma is identified. Stereotactic coordinates are measured (2.0 mm lateral to the bregma) for implantation of cells into the deep frontal white matter. A burr hole is drilled at this point and $1\times10^5$ GL261 cells are suspended in 5 µl of DMEM and are injected through a Hamilton syringe with a fixed, 25-gauge cannula at a depth of 3.0 mm relative to the dura mater. Injections are performed at 2.5 µl/min. The needle was withdrawn and the incision sutured. Kaplan-Meier survival plots are drawn and median survival times are determined for all groups. Survival differences are assessed for significance using the logrank Mantel-Cox method.

A summary of results from survival studies in the murine intracranial glioma model is provided in Table 3.

TABLE 3

| Peptide | Sequence | Result |
|---|---|---|
| DLAQMFFCFKELEGW (SVN53-67/57M) (SEQ ID NO: 6) | DC Vaccine = Median Survival of 53 days 2/8 100 day survivors | |
| DLAQMFFCFKELEGW (SVN53-67/57M) (SEQ ID NO: 6) | KLH Vaccine = Median Survival of 51 days 1/8 100 day survivor | |
| AQMFFCFKEL (SVN55-64/57M) (SEQ ID NO: 15) | DC Vaccine = Median Survival of 43 days | |
| QMFFCFKEL (SVN56-64/57M) (SEQ ID NO: 16) | DC Vaccine = Median Survival of 40 days | |
| MFFCFKEL (SVN57-64/57M) (SEQ ID NO: 17) | DC Vaccine = Median Survival of 29 days | |
| DLAQCFFCFKELEGW (SVN53-67) (SEQ ID NO: 18) | DC Vaccine = Median Survival of 57 days 2/8 100 day survivors | |
| CFFCFKEL (SVN57-64) (SEQ ID NO: 11) | DC Vaccine = Median Survival of 25 days | |

Figure 4:
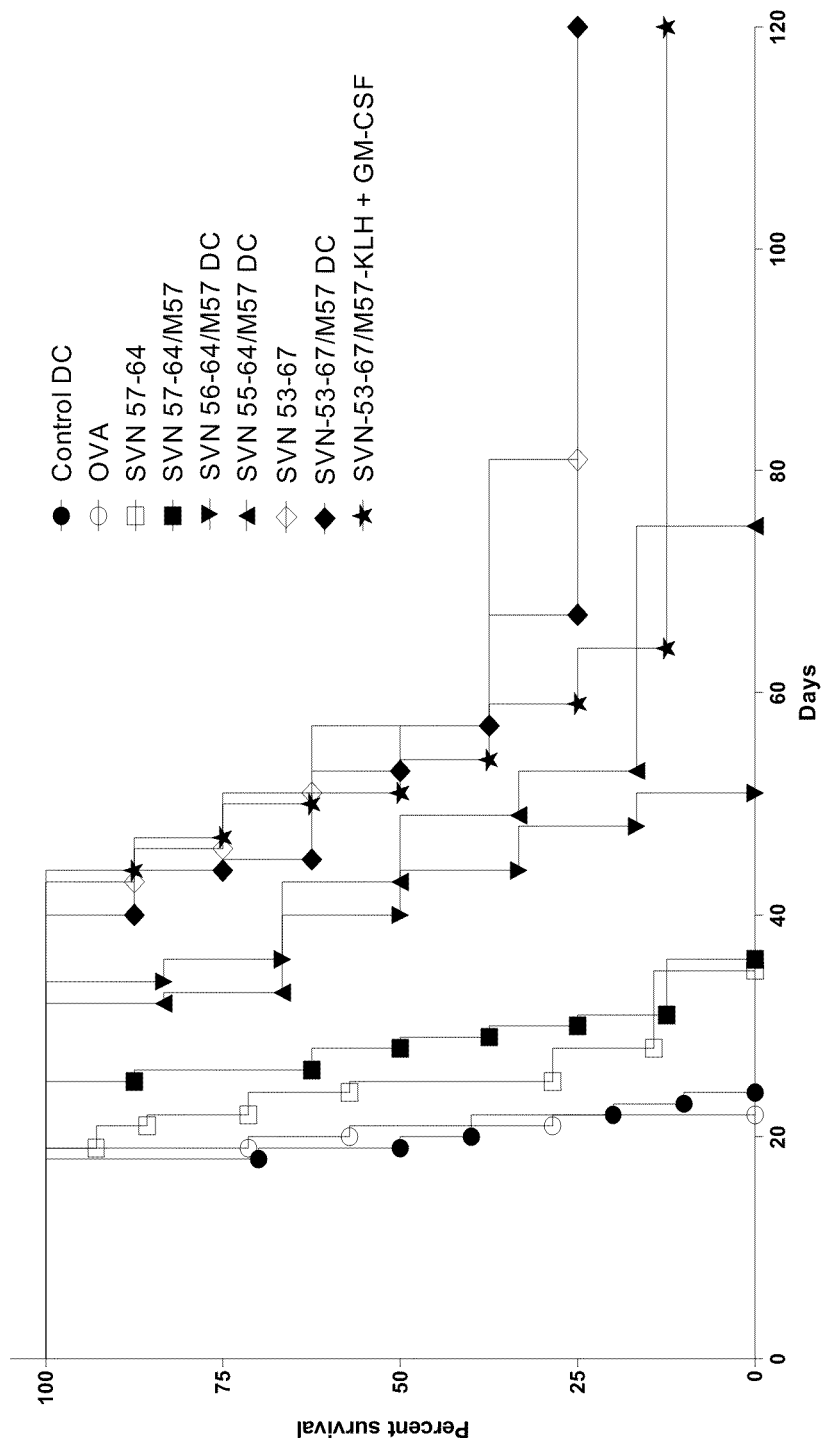
FIG. 4 provides a graphical representation of data obtained from intracranial survival studies in a GL261 murine model utilizing altered peptides based on survivin amino acids 53-67. The peptides were administered using peptide loaded dendritic cell (DC) vaccines or as Keyhole Limpet Hemocyanin (KLH) conjugates.

FIG. 4 provides a graphical summary of data from intracranial survival studies showing survival of C57BL6 mice with intracerebral GL261 glioma implants. To obtain the data presented in FIG. 4, mice were intracranially implanted with $1\times10^5$ GL261 cells and were treated with survivin peptide DC vaccines. C57BL/6 mice were immunized with SVN57-64 based altered peptides, or OVA258-265 peptide loaded DC2.4 cells as well as a direct subcutaneous injection of 100 ug SVN 53-67/M57-KLH peptide in Incomplete Freund's Adjuvant (IFA) plus 100 ng GM-CSF. Vaccinations began 4 days after tumor cell implantation and were repeated (boosted) every 7 days to simulate a therapeutic setting. Survival was plotted according to Kaplan-Meier methods. Long-term survivors were confirmed tumor-free by high field strength MRI.

As can be seen from Table 3 and FIG. 4, the peptide SVN57-64/M57 DC vaccine enhances survival moderately over the wild type peptide in the GL261-C57BL/6 glioma model. Importantly, both SVN53-67/M57 and SVN53-67 (wild type) confer 100% survival rates in mice for over 40 days when used as DC vaccines. SVN53-67/M57 was also tested as a KLH vaccine and resulted in a median survival of 51 days.

Figure 5:
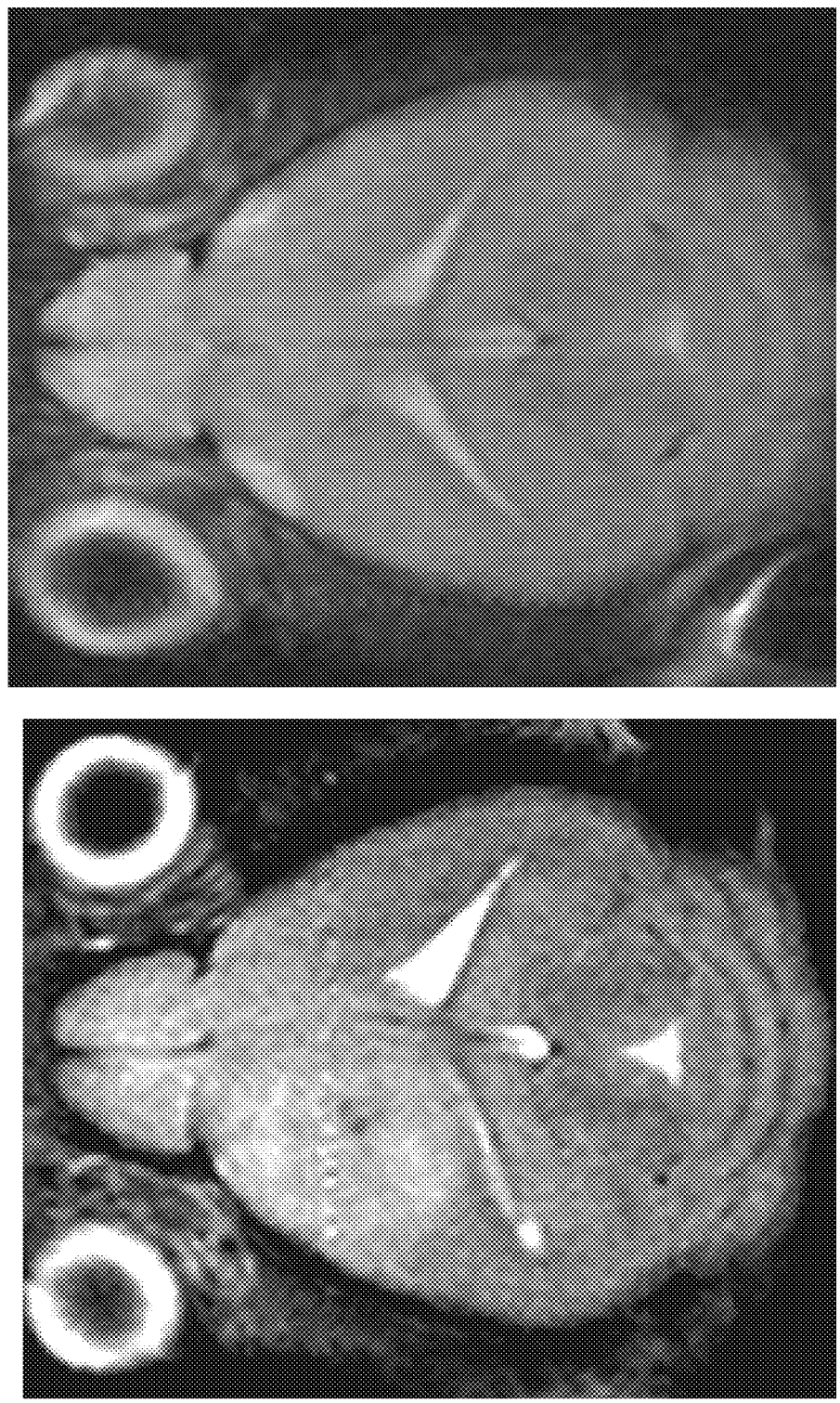
FIG. 5 provides a photographic representation of magnetic resonance imaging analysis from a mouse treated according to the method of the invention (right panel) and a negative control (left panel).

FIG. 5 provides a representative magnetic resonance image from a mouse from a survival curve shown in FIG. 4. Normally, a lethal tumor develops by day 18, as depicted in control mouse brain in left panel. Mice receiving SVN53-67/M57 peptide vaccine were still tumor free as of day 40. A small needle tract and residual scar tissue may be observed in the left frontal hemisphere in the vaccinated mouse image.

Thus, this Example demonstrates that the peptides of the invention are capable of enhancing survival and are potentially curative in a clinically relevant mouse model of glioma.

Example 3

This Example demonstrates enhanced MHC class I binding of the peptides of the invention relative to wild type peptides, and also demonstrates that the method of the invention can elicit an enhanced cell mediated immune response against human cancer cells that express survivin, including against non-glioma cancer cells.

Figure 9:
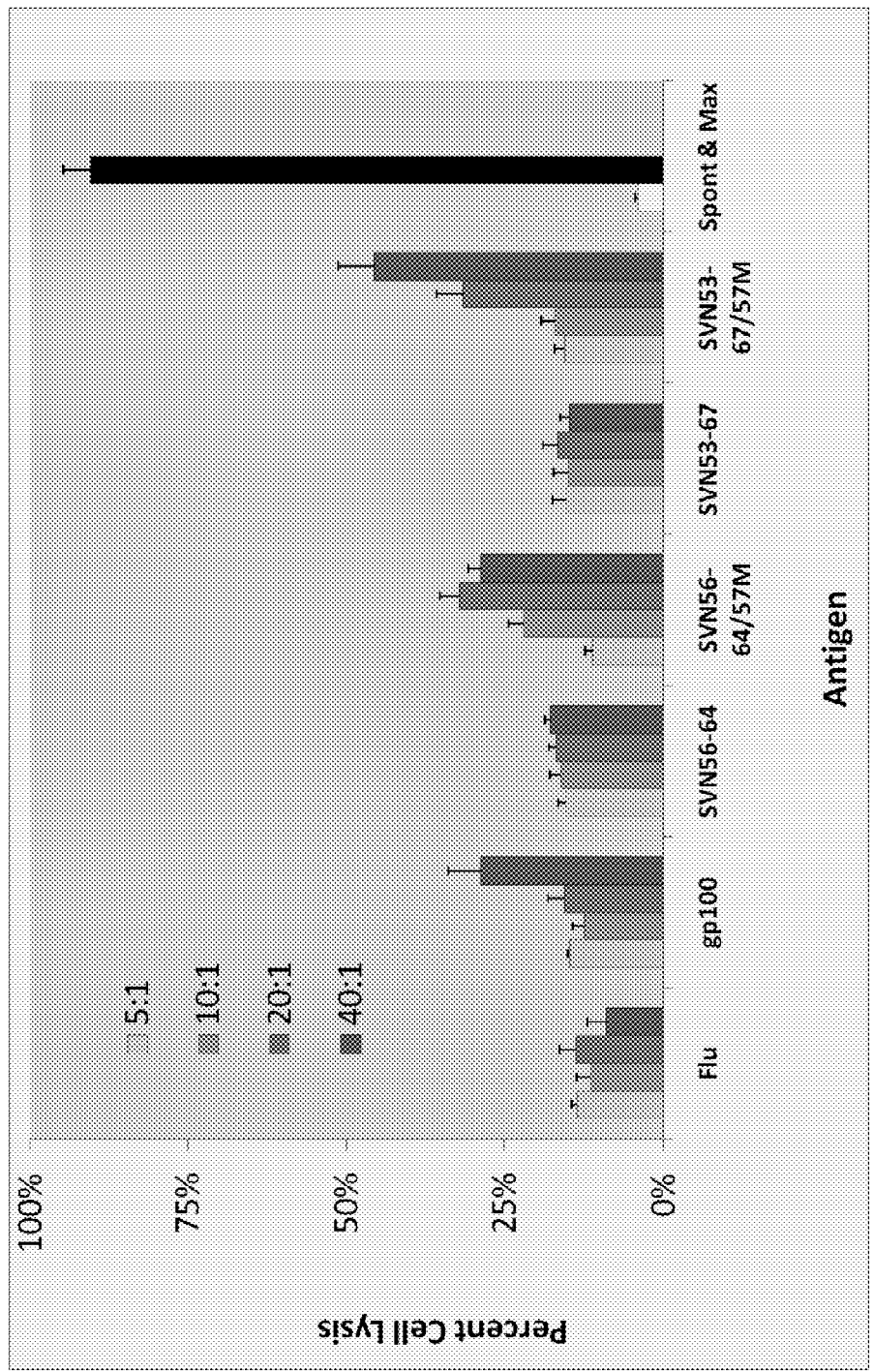
FIG. 9 provides a graphical representation of data obtained from ex vivo T cell stimulation via survivin-loaded autologous dendritic cells challenged with allogeneic U87 glioma (HLA-A*02; Allo-match).
Figure 10:
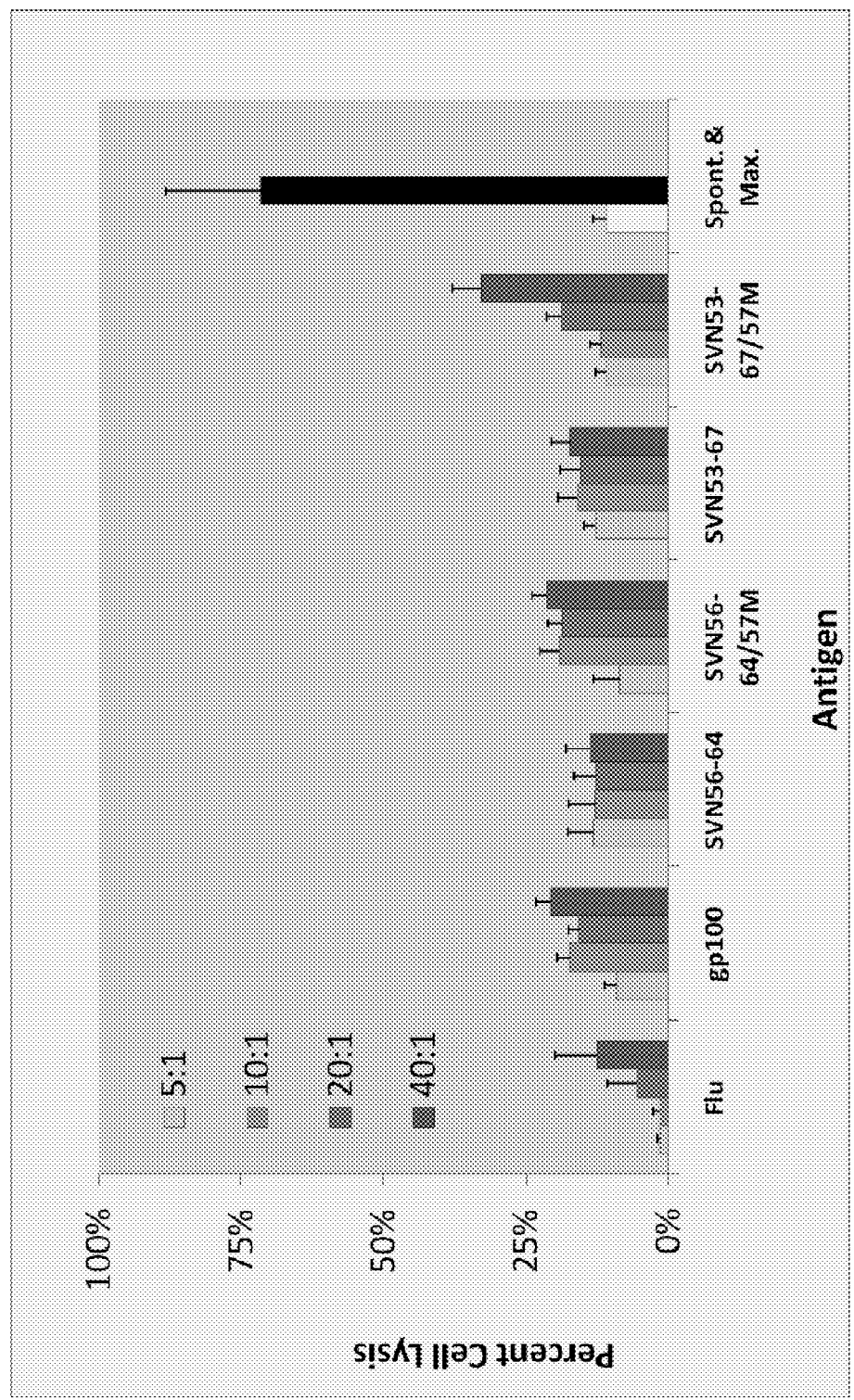
FIG. 10 provides a graphical representation of a second case wherein ex vivo T cell stimulation via survivin-loaded autologous dendritic cells challenged with allogeneic U87 Glioma was performed (HLA-A*02; Allo-match).
Figure 11:
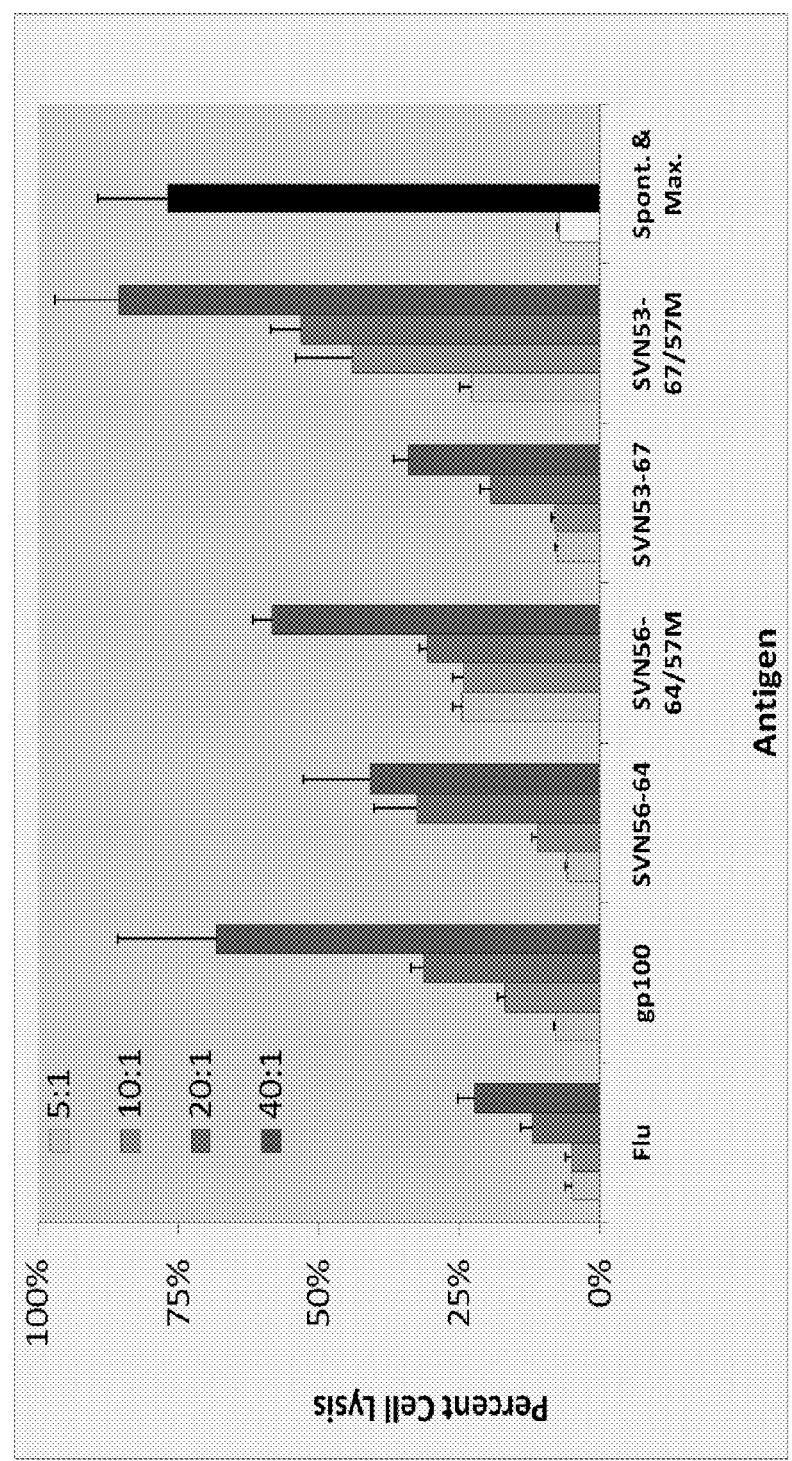
FIG. 11 provides a graphical representation of data obtained from ex vivo T cell stimulation via survivin-loaded autologous dendritic cells challenged with autologous glioma (HLA-A*03, HLA-A*29; Auto).
Figure 12:
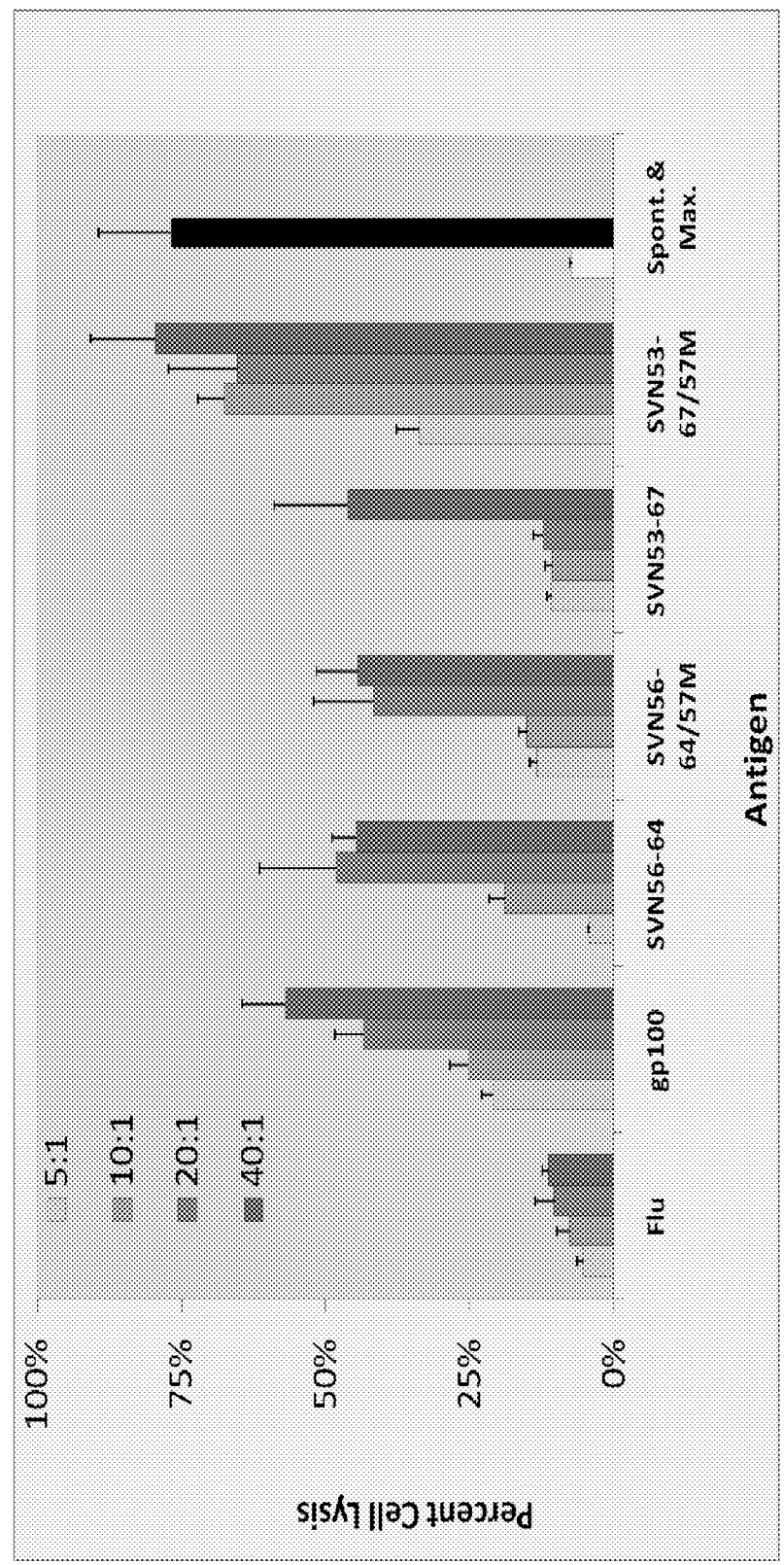
FIG. 12 provides a graphical representation of data obtained from ex vivo T cell stimulation via survivin-loaded autologous dendritic cells challenged with allogeneic DS-GBM Glioma (HLA-A*03; Allo-match).

Without intending to be bound by any particular theory, it is considered that SVN53-67/M57 and SVN53-67 exhibit similar survival profiles in C57BL/6 mice due to the M57 alteration not lying in an anchor position relative to the mouse H-2Kb molecule. As such, both peptides will bind H-2Kb (the murine MHC class I counterpart) to a similar extent in mice. The observation that SVN53-67/M57 retains the wild type immunogenic response in mice despite containing an alerted human epitope indicates that it is an effective peptide mimic (despite the fact that such an amino acid alteration could be expected to negatively impact immunity due to disruption of the interaction with the T cell receptor) and that the C to M alteration does not impart deleterious effects when SVN53-67/M57 is used as a vaccine. However, it is in administration to humans that the peptides of the invention are expected to display their enhanced potential, since the alteration of 57C to M alters the wild type peptide so that it contains a sequence that facilitates improved interaction with human MHC I. This is supported by the disparate MHC class I binding characteristics of the wild type and M57 peptides (FIG. 6A-C). As determined by competitive peptide binding assays, SVN53-67/M57 binds HLA-A*0201 approximately 12 fold stronger than the wild type SVN53-67 (FIG. 6A-B). Moreover utilizing a survivin/MHC Class I-specific pentamer, the core peptide SVN56-64/M57 binds HLA-A*0201 approximately 73 fold stronger than the wild type SVN56-64 (FIG. 6C). Collectively, this signifies that the C>M alteration leads to enhanced affinity of peptide mimic for the MHC class I molecule relative to the wild type survivin sequence. Thus, the C to M change elicits a profound improvement in MHC class I binding over the wild type sequence. This improvement would be expected to result in enhanced CTL activation against autologous cancer cells. It is accordingly noteworthy that, as compared to the wild type peptide, SVN53-67/M57 elicits a 3 to 5 fold increase in CTL mediated killing against allogeneic HLA-matched human glioma (FIGS. 9-10), autologous human glioma (FIGS. 11-12) and autologous human lymphoma cells (FIG. 13), demonstrating that the method of the invention can elicit a cell mediated immune response that is significantly improved over that induced by peptides having a wild type sequence. Moreover, the data in FIG. 13 demonstrate that the method of the invention can elicit a cell mediated immune response against human cancer cells other than glioma. Thus, the method is expected to have broad applicability against all types of cancer cells that express survivin.

Example 4

This Example demonstrates ex vivo T cell stimulation using survivin-loaded autologous human dendritic cells challenged with human U87 glioblastoma or human lymphoma cells. Data obtained from these challenges are presented in FIGS. 8-13.

To produce the data presented in FIGS. 8-13, CTL assays for specific T cell lysis of target cells were performed using the Live/Dead cell mediated cytotoxicity method using flow cytometry. Patient-derived Peripheral Blood Monocyte Cells (PBMC) were cultured into DC ex vivo in the presence of GM-CSF and IL-4. After 5-6 days of differentiation into immature DC, specific peptides were added along with CD-40L to stimulate and develop mature DC. Post-maturation additional autologous PBMC were added and allowed to develop into CTL's. After 10 days cells were removed and mixed with autologous or allogeneic human glioma cells in culture to assess cell killing ability of CTL's. CTL were added to the target glioma cells in ratios ranging from 5:1 to 40:1 for 2 hours at 37° C. The analysis is based upon gating of labeled glioma cells to eliminate background from effector cells. Maximal cytotoxicity was simulated using ethanol-treated target cells. Spontaneous cytotoxicity represents target cells incubated in the absence of effector cells. Flu and gp100 peptide stimulations represent additional stimulation controls. Data represent mean percent specific lysis±S.E.M. of triplicate samples.

Figure 13:
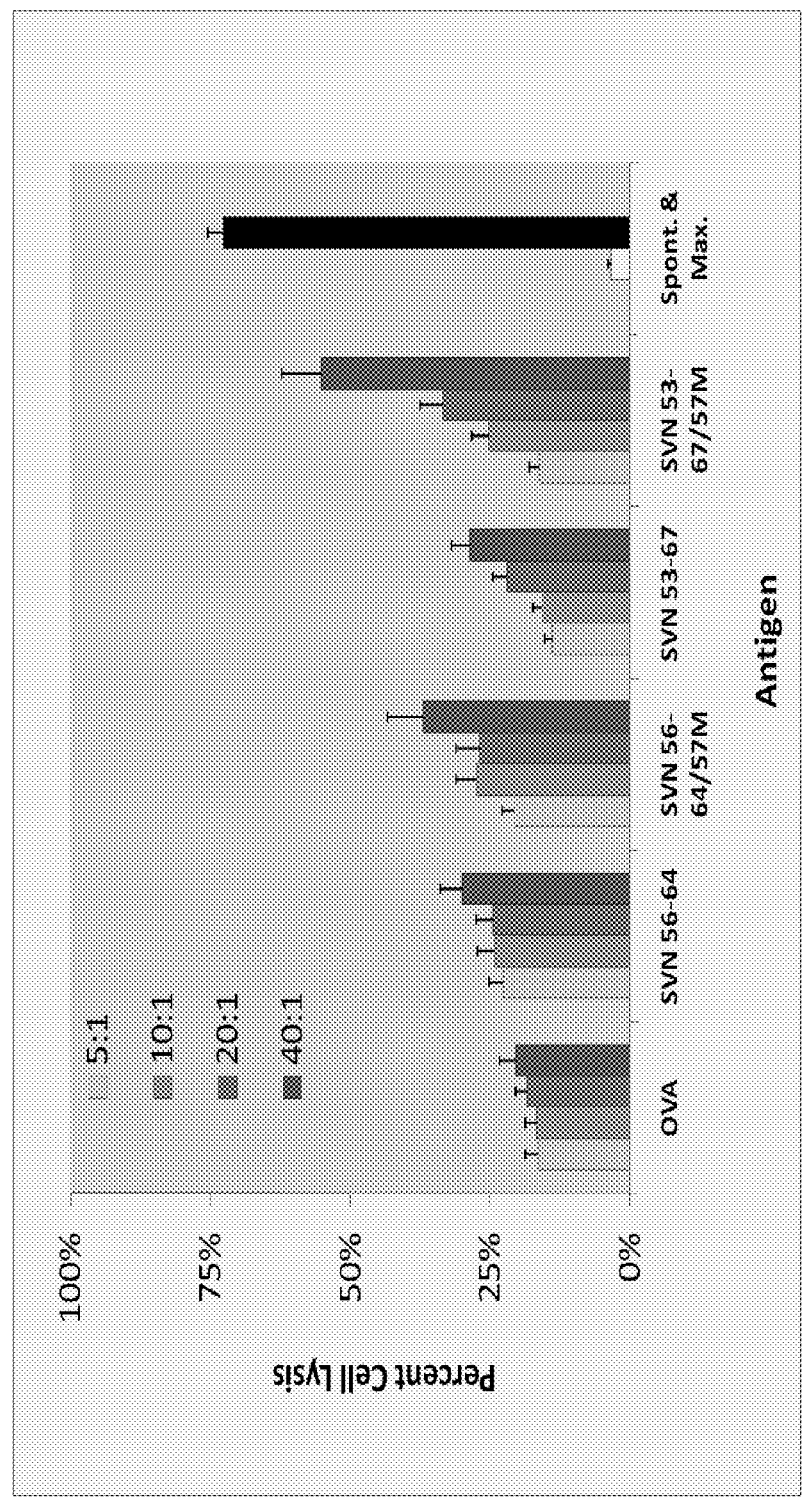
FIG. 13 provides a graphical representation of data obtained from ex vivo T cell stimulation via survivin-loaded autologous dendritic cells challenged with autologous CNS Lymphoma (HLA-A*2901, HLA-A*3002; Auto).

The data presented in FIG. 13 was obtained in essentially the same manner as for FIGS. 9-12, with the exception that the effect of CTLs on autologous CNS lymphoma cells (rather than on autologous or allogenic glioma) was analyzed.

The data presented in FIGS. 9-12 demonstrate the efficacy of the peptides of the invention in eliciting a strong cell mediated immune response against allo-matched or autologous gliomas. Therefore, the method of the invention is expected to elicit a similar response when administered to an individual. Importantly, a strong cell mediated immune response was also generated against autologous CNS lymphoma cells (FIG. 13), demonstrating that the peptides of the invention are not limited to being capable of eliciting a cell mediated response against only glioblastoma cells.

Thus, based on the foregoing data, the method of the present invention is expected to elicit an effective cell mediated immune response against any type of survivin expressing cancer cell in an individual and accordingly, inhibit the growth of such cancer cells.

The invention has been described through specific embodiments. However, routine modifications to the compositions, methods and devices will be apparent to those skilled in the art and such modifications are intended to be covered within the scope of the invention.

We claim:

1. A peptide of SEQ ID NO:4 (ENEPDLAQM-FFCFKELEGWEPDD) or a fragment thereof, wherein the fragment comprises at least 9 contiguous amino acids of SEQ ID NO:4, and wherein the fragment comprises the sequence of SEQ ID NO:5 (QMFFCF).

2. The peptide of claim 1, wherein the peptide consists of a sequence selected from the group of sequences consisting of SEQ ID NO:6, SEQ ID NO:15, and SEQ ID NO:16 and SEQ ID NO:17.

3. The peptide of claim 1, wherein the peptide consists of the sequence of SEQ ID NO:6. (DLAQMFFCFKELEGW).

4. The peptide of claim 1, wherein the peptide is conjugated to an immunogenic protein carrier.

5. A substantially purified population of mammalian dendritic cells, wherein the dendritic cells have been incubated with a peptide of claim 1, such that the peptide is taken up by the dendritic cells.

6. The dendritic cells of claim 5, wherein the peptide consists of the sequence of SEQ ID NO:6.

7. A composition comprising the peptide of claim 1.

8. The composition of claim 7, wherein the composition further comprises dendritic cells that have been incubated with the peptide.

9. The composition of claim 7, further comprising an adjuvant.

10. A method for inhibiting growth of cancer cells in an individual diagnosed with or suspected of having cancer, wherein the cancer cells express survivin, the method comprising administering a composition of claim 7 to the individual, wherein the growth of the cancer cells is inhibited subsequent to said administration.

11. The method of claim 10, wherein the individual has been diagnosed with a glioma.

12. The method of claim 10, wherein the individual has been diagnosed with lymphoma.

13. The method of claim 10, wherein the peptide in the composition is conjugated to an immunogenic carrier protein.

14. The method of claim 10, wherein the peptide in the composition consists of the sequence of SEQ ID NO:6.

15. The method of claim 10, wherein the peptide in the composition is present in dendritic cells that have taken up the peptide.

16. The method of claim 10, wherein the cancer cells are present in a tumor.

17. The method of claim 16, wherein the composition is administered subsequent to resection of the tumor.

18. The method of claim 10, wherein the administration of the composition stimulates a cell mediated immune response against survivin in the individual.

* * * * *

UNITED STATES PATENT AND TRADEMARK OFFICE
CERTIFICATE OF CORRECTION

| | | |
|---|---|---|
| PATENT NO. | : 7,943,138 B2 | |
| APPLICATION NO. | : 12/176052 | |
| DATED | : May 17, 2011 | |
| INVENTOR(S) | : Ciesielski et al. | |

It is certified that error appears in the above-identified patent and that said Letters Patent is hereby corrected as shown below:

In the Specification

Column 1, lines 6-8 should read:

--STATEMENT AS TO FEDERALLY SPONSORED RESEARCH

This invention was made with government support under NS049309 awarded by the National Institute of Health. The government has certain rights in the invention.--

Signed and Sealed this
Twenty-ninth Day of March, 2016

Michelle K. Lee
*Director of the United States Patent and Trademark Office*